United States Patent
Shinyama

(10) Patent No.: US 8,754,938 B2
(45) Date of Patent: Jun. 17, 2014

(54) SOLDER PRINTING INSPECTION APPARATUS AND SOLDER PRINTING SYSTEM

(75) Inventor: Takayuki Shinyama, Aichi (JP)

(73) Assignee: CKD Corporation, Aichi (JP)

( * ) Notice: Subject to any disclaimer, the term of this patent is extended or adjusted under 35 U.S.C. 154(b) by 667 days.

(21) Appl. No.: 13/006,101

(22) Filed: Jan. 13, 2011

(65) Prior Publication Data

US 2011/0216186 A1  Sep. 8, 2011

(30) Foreign Application Priority Data

Mar. 3, 2010  (JP) .................................. 2010-46318

(51) Int. Cl.
  *G01N 21/88* (2006.01)
(52) U.S. Cl.
  USPC ........................................... 348/126; 348/125
(58) Field of Classification Search
  None
  See application file for complete search history.

(56) References Cited

U.S. PATENT DOCUMENTS

2009/0202143 A1 * 8/2009 Mamiya ........................ 382/150

FOREIGN PATENT DOCUMENTS

| JP | 6-331327 A | | 12/1994 |
|---|---|---|---|
| JP | 06331327 A | * | 12/1994 |
| JP | 2002-361830 A | | 12/2002 |
| JP | 2004-317291 A | | 11/2004 |
| JP | 2004317291 A | * | 11/2004 |
| JP | 2005-223281 A | | 8/2005 |
| JP | 2005223281 A | * | 8/2005 |

OTHER PUBLICATIONS

Office Action issued in Japanese Application No. 2010-046318, dated Jan. 10, 2012 (9 pages).

* cited by examiner

*Primary Examiner* — Mehrdad Dastouri
*Assistant Examiner* — James Anderson, II
(74) *Attorney, Agent, or Firm* — Osha Liang LLP

(57) ABSTRACT

A solder printing inspection apparatus for inspection of solder printed on a circuit board has a multiplicity of lands for mounting of electronic components. The apparatus includes an irradiation unit for irradiating a light on the circuit board, an imaging unit for imaging the circuit board irradiated by the light, a solder bridge detection unit for detecting a solder bridge connecting two of the lands based on an image data imaged by the imaging unit, a distance calculation unit for calculating a bridge distance as distance between two lands contacting the solder bridge or solder bridging regions or solder detection frames corresponding to the two lands contacting the solder bridge, and a distance determination unit for determination of whether or not the bridge distance is within a permissible range.

3 Claims, 6 Drawing Sheets

SOLDER PRINTING INSPECTION APPARATUS AND SOLDER PRINTING SYSTEM

CROSS-REFERENCE TO RELATED APPLICATIONS

This Application claims priority to Japanese Patent Application No. 2010-46318 filed on Mar. 3, 2010 in Japan.

BACKGROUND OF INVENTION

1. Field of the Invention

The present invention generally relates to a solder printing apparatus for inspection of solder printed on a printed circuit board and also relates to a solder printer system equipped with the solder printing apparatus.

2. Background Art

In order to mount electronic components on a printed circuit board, generally cream solder is first printed by a solder printer on multiple lands formed on the printed circuit board. Next, the electronic components are provisionally set on the printed circuit board using the viscosity of this cream solder. Thereafter, the above-described printed circuit board is loaded into a reflow furnace and is subjected to a certain reflow process to perform soldering.

Solder bridges may be formed during this type of soldering, and such solder bridges cause shorts between multiple lands. Therefore, after the solder printing process, the printed circuit board is inspected (see, e.g., Japanese Unexamined Laid-open Patent No. 2005-223281) to determine whether or not printing on the various lands has been properly performed. Then, if a solder bridge has been detected, a maintenance operation is performed, e.g., stoppage of the solder printer, cleaning or maintenance of the solder printer, or the like (see, e.g., Japanese Unexamined Laid-open Patent No. 2002-361830).

However, the presence or absence of such a solder bridge has been previously detected by inspecting only parts of the circuit board where the distance between lands is relatively short and where the occurrence of solder bridging is relatively easy. Among the solder bridges detected by this type of inspection, many solder bridges occur accidentally and as isolated events that are unrelated to whether operating conditions of the solder printing apparatus are good or bad. For this reason, there is concern that, if the solder printing apparatus is stopped every time such a minor solder bridge is detected and, performing the inspection operation would result in frequent stoppages of the manufacturing line and a marked worsening of productivity.

In order to prevent this worsening of productivity, a configuration has been considered, for example, that remembers the count of detected solder bridges and stops the solder printing apparatus only if the detected count exceeds a certain value. If some sort of major problem occurs, such as contamination of the metal mask, the frequency of occurrence of solder bridging greatly increases. Further, solder printing is continued under such conditions without performing maintenance on the solder printing apparatus, numerous printed boards with printing defects would be manufactured until the detected solder bridge count reaches a certain value, and yield dramatically declines.

SUMMARY OF INVENTION

In one or more embodiments, the present invention provides a solder printing inspection apparatus and a solder printing system capable of suppressing lowering of productivity when performing solder printing.

In a first aspect of the claimed invention, a solder printing inspection apparatus for inspection of solder printed on a circuit board may have a multiplicity of lands for mounting of electronic components. The solder printing inspection apparatus includes an irradiation unit that irradiates a light on the circuit board, an imaging unit that images the circuit board irradiated by the light, a solder bridge detection unit that detects a solder bridge connecting two of the lands based on an image data imaged by the imaging unit, a distance calculation unit that calculates a bridge distance as distance between two lands contacting the solder bridge or solder bridging regions or solder detection frames corresponding to the two lands contacting the solder bridge, a distance determination unit that determines whether or not the bridge distance is within a permissible range, and a severe defect processing unit that performs a certain severe defect processing when the bridge distance is determined not to be within the permissible range.

The above-described "certain severe defect processing" may include, for example, notification processing by indicating the occurrence of some type of malfunction, output processing by outputting to the solder printing apparatus various types of signals as feedback indicating that such a malfunction has occurred, and the like.

A solder bridge having a bridge distance exceeding the permissible range in the above-described manner is not a minor solder bridge, but rather is a solder bridge having a high probability of being caused by a malfunction of the solder printing apparatus. Therefore, inspection of the solder printing apparatus is needed when such a solder bridge is detected.

Thus, when even a single severe solder bridge having a bridge distance exceeding the permissible range is detected as per the above-described first aspect, if various types of severe defect processing are performed immediately in the above-described manner, then, it becomes possible to prevent a situation in which production continues for a long time interval while the solder printing apparatus malfunctions. This reduces the generation of defective products and allows for an improvement of yield.

On the other hand, because the present aspect is arranged such that severe defect processing is performed only when a severe solder bridge has been detected, the solder printing apparatus is not stopped unnecessarily every time a comparatively minor solder bridge is detected (e.g., a solder bridge having a bridge distance within the permissible range), and useless inspection processing is not performed. This makes an improvement of productivity possible.

In a second aspect of the claimed invention, a solder printing inspection apparatus for inspection of solder printed on a circuit board may have a multiplicity of lands for mounting of electronic components. The solder printing inspection apparatus includes an irradiation unit that irradiates a light on the circuit board, an imaging unit that images the circuit board irradiated by the light, a solder bridge detection unit that detects a solder bridge connecting at least two of the lands based on an image data imaged by the imaging unit, a detection unit that extracts two lands, solder printing regions (or solder inspection frames having a farthest positional relationship among at least two lands contacting a single solder bridge or a solder printing region or solder inspection frame set corresponding to such lands), a distance calculation unit that calculates, as a bridge distance, a minimum distance between the extracted two lands, solder printing regions, or solder inspection frames, a distance determination unit that determines whether or not the bridge distance is within a permissible range, and a severe defect processing unit that performs a certain severe defect processing when the bridge distance is determined not to be within the permissible range.

In addition to having an operational effect similar to that of the above-described first aspect, this second aspect of the claimed invention is especially excellent with respect to the below-described points.

For example, when a BGA (Ball Grid Array) or the like IC package is being mounted, small lands are densely arranged on the circuit board with extremely narrow gaps. Therefore, solder bridging readily occurs due to even an extremely small solder bridge. When using a method for pass-fail determination based on the conventional method of inspection of the state of the solder printed on a circuit board having a high density of lands in this manner (e.g., when using a method based only on detection of whether or not a solder bridge is present between two adjacent lands), there is concern that the issues described above in the "Background Art" would become more severe.

In contrast, according to the second aspect of the claimed invention, two lands or the like having the closest positional relationship among the multiple lands or the like contacting a single solder bridge are extracted. That is, relatively severe solder bridges present on multiple lands are extracted. Also, this second aspect is configured such that severe defect processing is performed only when the solder bridge is relatively large. This has the result of eliminating frequent stoppage of the solder printing apparatus and making an improvement of productivity possible.

In a third aspect of the claimed invention, the solder printing inspection apparatus may further include a memory unit that remembers various types of setting data relating to manufacture of the circuit board, and the solder bridge detection unit, based on the setting data, sets a bridge inspection frame for detection of the solder bridge.

According to the third aspect of the claimed invention, in comparison to a configuration that sets the bridge inspection frame based on various types of data extracted from the image data imaged by the imaging unit, the processing procedure becomes simplified and faster, and this results in an ability to improve inspection efficiency and, thus, productivity.

In alternative embodiments in the third aspect of the claimed invention, the solder printing inspection apparatus may include a memory unit that remembers various types of setting data relating to the manufacture of the circuit board, and for the distance detection unit that calculates the bridge distance based on the design data. Further, alternatively, the above type of result can be obtained by having the solder printing inspection apparatus further include memory unit that remembers various types of setting data relating to the manufacture of the circuit board, and having the detection unit extracts two lands, solder printing regions, or solder inspection frames having a farthest positional relationship. Also, the solder printing inspection apparatus may further include a memory unit that remembers various types of setting data relating to the manufacture of the circuit board, and for the detection unit that extracts two lands, solder printing regions, or solder inspection frames having a farthest positional relationship based on the design data.

In a forth aspect of the claimed invention, the solder printing inspection apparatus may further include a display unit that displays the detection counts of the solder bridges separately according to the bridge distance.

According to the above-described forth aspect of the claimed invention, by display of the detection count of solder bridges separately according to bridge distance, trends in the occurrence of solder bridges can be readily understood, and such trend data can be used when adjusting the solder printing apparatus or the like. When a solder bridge has been detected having a bridge distance outside of the permissible range, this also has the effect of making possible recognition at a single glance that a such a solder bridge has been detected. Such display processing may be used as the above-described severe defect processing. In addition, a configuration may be adopted that is capable of displaying multiple time series of detection results of a certain detection time interval or a certain detection unit. The trends of the occurrence of solder bridges are more easily understood by adoption of this type of configuration.

In a fifth aspect of the claimed invention, a solder printing system may include a solder printing apparatus for printing of solder and the solder printing inspection apparatus according to any one of the above-described aspects 1-4. The severe defect processing unit outputs a certain malfunction signal to the solder printing apparatus as the severe defect processing; and the solder printing apparatus performs a certain processing when the malfunction signal has been input.

The fifth aspect of the claimed invention may have an operational effect similar to that of the above-described first aspect. Furthermore, the "certain processing" is exemplified by processing to stop the solder printing operation, processing to clean the screen used for printing (e.g., the metal mask), and the like.

Other aspects and advantages of the invention will be apparent from the following description and the appended claims.

DETAILED DESCRIPTION

Embodiments of the present invention are explained below, referring to the attached figures. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention.

Figure 1:
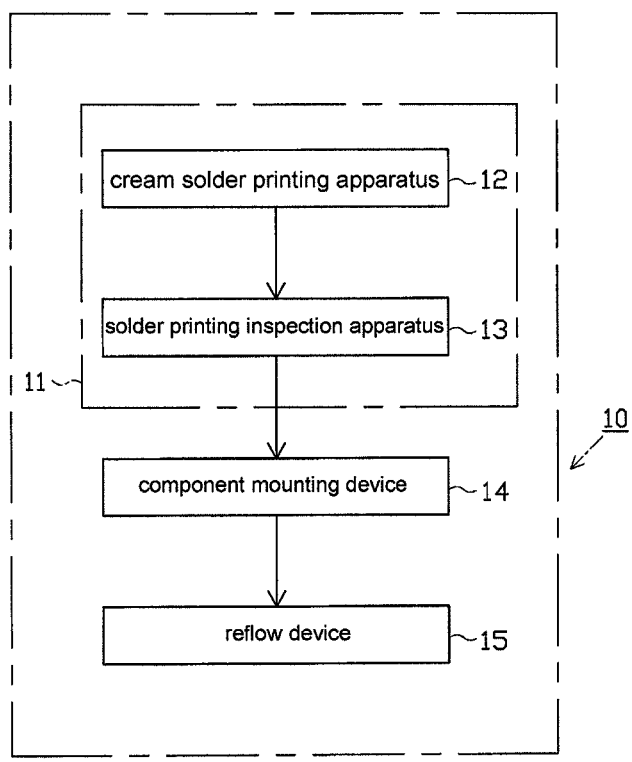
FIG. 1 shows schematically part of the manufacturing line of the printed circuit board according to one or more embodiments of the present invention.

FIG. 1 is a simplified drawing showing schematically part of the manufacturing line of a printed circuit board according to one or more embodiments of the present invention.

Figure 2:
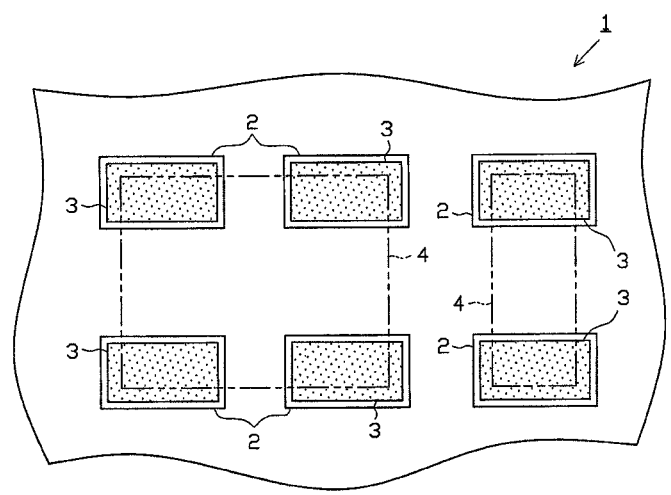
FIG. 2 shows a schematic drawing for explanation of the configuration of the printed circuit board according to one or more embodiments of the present invention.

Firstly, structure of the printed circuit board will be explained. As shown in FIG. 2, a printed circuit board 1 (abbreviated hereinafter as the "circuit board") has multiple lands 2. In addition to viscous cream solder (abbreviated hereinafter as "solder") being printed on the land 2, an electronic component 4, such as a chip and the like, is carried on the solder 3. The electronic component 4 is equipped with multiple electrodes and leads (not illustrated), and the various electrodes and leads are connected to certain respective solders 3. In FIG. 2 and other figures for convenience, a dot pattern is used in parts indicating solder.

The manufacturing system of the circuit board 1 will be explained next. As shown in FIG. 1, the circuit board manufacturing system 10 of the present embodiment, in order from the upstream side (i.e., left side), is equipped with a solder printing system 11, a component mounting apparatus 14, and a reflow device 15.

The solder printing system 11 is equipped with a cream solder printing apparatus 12 and a solder printing inspection apparatus 13.

The cream solder printing apparatus 12 (referred to hereinafter simply as the "solder printing apparatus") is used for printing a certain amount of the solder 3 on the land 2 of the circuit board 1. More specifically, the solder printing apparatus 12 is equipped with a metal mask (not illustrated) having aperture parts formed at positions corresponding to each of the lands 2 on the circuit board 1, and the solder printing apparatus 12 uses this metal mask for screen printing of the solder 3 on the circuit board 1.

The solder printing inspection apparatus 13 is used for inspection of the printed solder 3. The solder printing inspection apparatus 13 is explained below in detail.

The component mounting apparatus 14 is used for mounting the electronic component 4 on the printed solder 3. The reflow device 3 is used for heating and melting the solder so that connections are made between the land 2 and the electrodes or leads of the electronic component 4.

Figure 3:
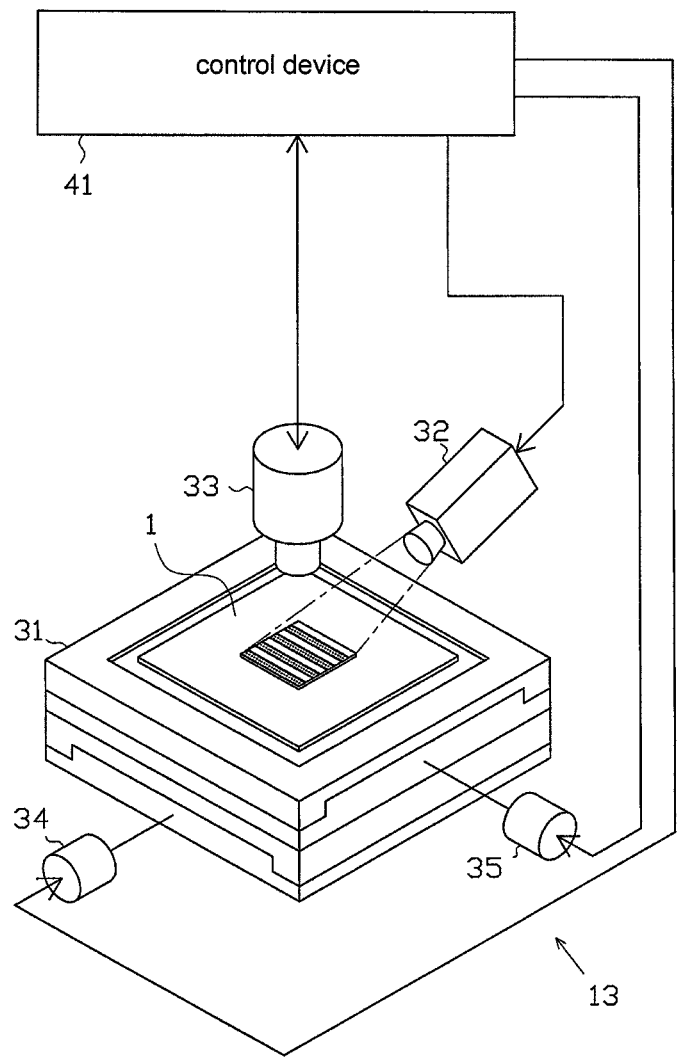
FIG. 3 shows a simplified structural drawing schematically showing the solder printing inspection apparatus according to one or more embodiments of the present invention.

As shown in FIG. 3, a control device 41 is provided for calculation processing and for performance of control of various components (e.g., a carrying stage for carrying the circuit board 1, an illumination device 32 as the irradiation unit (irradiation for three dimensional measurement), and a CCD camera as the imaging unit, or the like).

Motors 34 and 35, which have mutually orthogonal rotational axes, are provided on the carrying stage 31. Due to drive control of these motors 34 and 35 by the control device 41, the circuit board 1 carried on the carrying stage 31 can be slid in an arbitrary direction along the X-axis and Y-axis. It is possible by this means to cause relative movement of the visual field of the CCD camera 33.

The illumination device 32 is constructed so as to be capable of using a certain light pattern to illuminate the surface of the circuit board 1 from a tilted angle.

The CCD camera 33 is arranged directly above the circuit board 1 so as to be capable of imaging the part of the circuit board 1 illuminated by the above-described light pattern. The image data imaged by this CCD camera 33 is converted into a digital signal within the CCD camera 33 and is sent in the form of a digital signal as input to the control device 41.

Based on this image data, the control device 41 performs image processing, inspection processing, and the like in the below-described manner.

Figure 4:
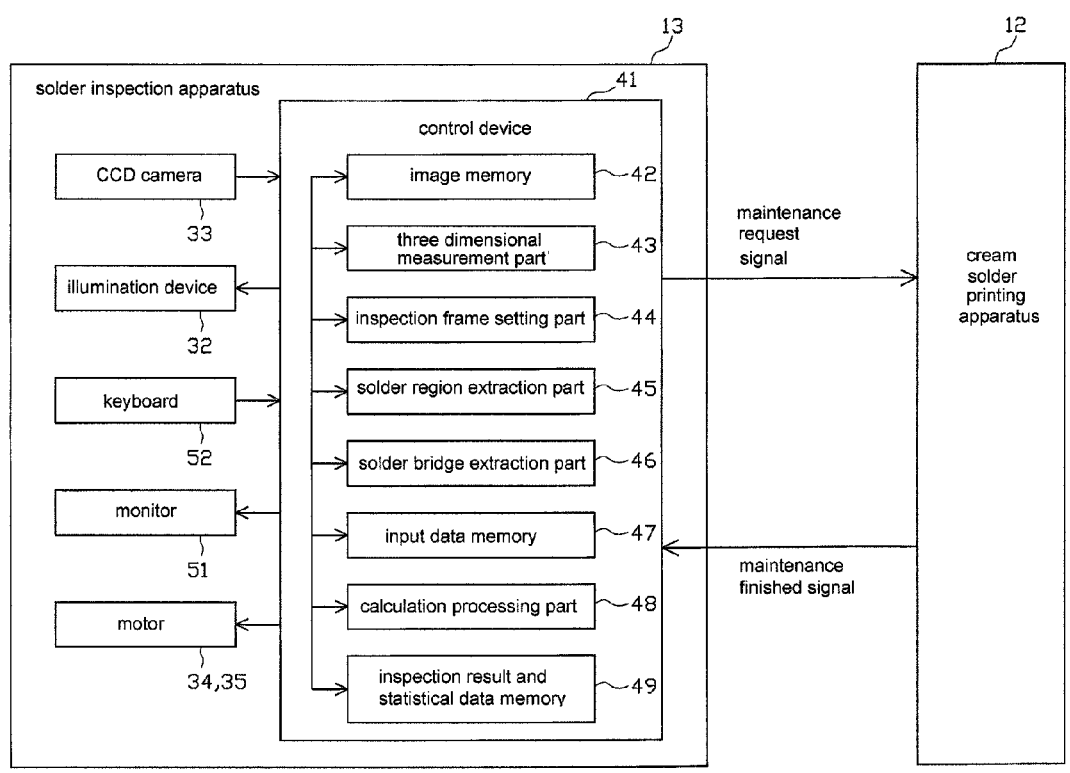
FIG. 4 shows a simplified structural drawing schematically showing the solder printing system according to one or more embodiments of the present invention.

This control device 41 will be explained next in detail. As shown in FIG. 4, the control device 41 is equipped with an image memory 42, a three dimensional measurement part 43, an inspection frame setting part 44 (e.g., inspection frame setting unit), a solder region extraction part 45, a solder bridge extraction part 46, an input data memory 47 (e.g., memory unit), a calculation processing part 48, and an inspection result and statistical data memory 49.

The image data imaged by the CCD camera 33 are stored sequentially in the image memory 42.

Based on the image data stored in the image memory 42, the three dimensional measurement part 43 performs three dimensional measurement (e.g., mainly measurement of height) of the solder 3 printed on the circuit board 1. In the present embodiment, the printed condition of the solder 3 is inspected based on the height data and the like of the solder 3 obtained in this manner. Although the phase shift method is adopted in the present embodiment for performance of the three dimensional measurement, any other measurement method can be adopted, as exemplified by the light-section method, spatial encoding method, focusing method, or the like.

The inspection frame setting part 44 has a function for setting various types of inspection frames in the image data stored in the image memory 42 during inspection of the printed condition of the solder 3. For example, a solder inspection frame W2 (see, FIG. 6) is set based on the solder printing area W1 in order to inspect positional displacement or missing areas of the solder 3. In order to examine whether or not a solder bridge 3b (see, FIGS. 7 and 8) is present between multiple lands 2, the bridge inspection frame W3 is set between the solder printing regions W1 upon a combination of lands 2. Setting of the various types of frames is performed based on circuit board design data such as Gerber data or the like stored beforehand in the input data memory 47.

The solder region extraction part 45 has a function for detection of solder clumps exceeding a certain height and exceeding a fixed surface area within the bridge inspection frame W3.

The solder bridge extraction part 46 has a function for determination of whether or not a solder clump within the bridge inspection frame W3 is a solder bridge 3b. Detection of the solder bridge 3b, for example, is performed by determination of whether or not a connecting solder clump is present that connects together both solder inspection frames W2 setup at two lands 2. Other methods may be adopted for detection of the solder bridge 3b.

The solder bridge detection unit of the present embodiment includes the functions of the three dimensional measurement part 43, the inspection frame setting part 44, the solder region extraction part 45, and the solder bridge extraction part 46.

The input data memory 47 stores various types of previously input data and the like relating to the manufacture of the circuit board 1. Design data stored in the input data memory 47 include, for example, the position or size of the land 2 on the circuit board 1, the solder printing region W1, size of the solder 3 under ideal printing conditions, size of the circuit board 1, and the like.

The calculation processing part 48 performs various types of calculation processing and determination processing related to inspection. For example, the calculation processing part 48 in the below-described manner performs processing to extract multiple lands 2 connected by a single solder bridge 3b, processing to calculate the bridge distance Lx (e.g., minimum distance between such two lands), processing to determine whether or not this bridge distance Lx is within the permissible range, and the like.

Coordinate, etc. data relating to image data, calculation results calculated by the calculation processing part 48, statistical data obtained by statistical processing of the inspection data, and the like are stored in the inspection result and statistical data memory 49.

The control device 7 is connected to a monitor 51 (e.g., display unit), a keyboard 52 (e.g., data input unit), the solder printing apparatus 12, and the like. The control device 7 has a function for performing input-output control of various types of data and signals between these components. According to this function, for example, image data stored in the image memory 42, various types of data stored in the inspection result and statistical data memory 49, and the like can be displayed on an appropriate monitor 51. Also, various types of signals can be exchanged with the solder printing apparatus 12 as explained below.

Figure 5:
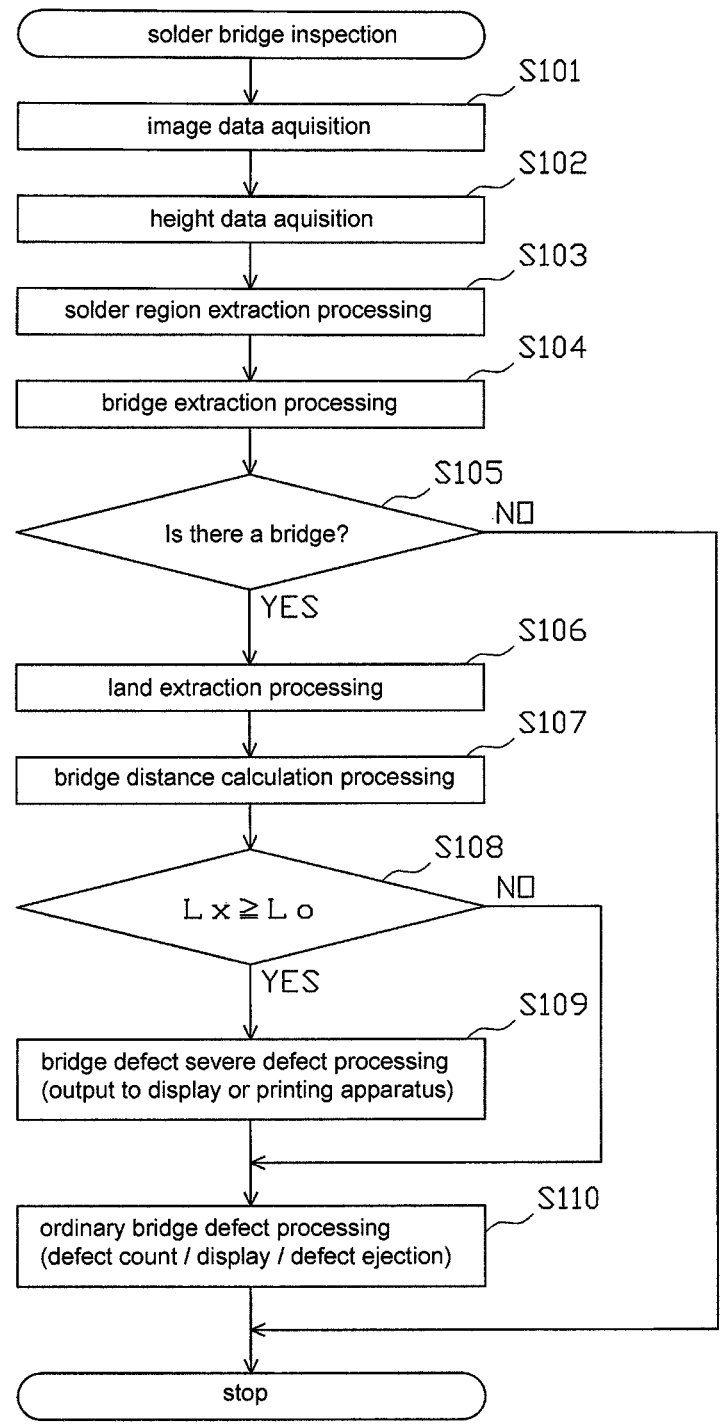
FIG. 5 shows a flow chart for explanation of the details of processing during solder bridge inspection according to one or more embodiments of the present invention.

Among various types of solder inspection performed by the solder printing inspection apparatus 13, solder bridge inspection will be explained next in detail while referring to FIG. 5. FIG. 5 is a flow chart showing details of the solder bridge inspection.

As shown in FIG. 5, firstly image data of the circuit board 1 (e.g., the object undergoing inspection) are obtained during step S101. Specifically, when a certain light pattern from the illumination device 32 is irradiated, the circuit board is moved sequentially by the motors 34 and 35. The entire circuit board 1 is imaged using the CCD camera 33, and this image data is stored in the image memory 42.

Thereafter, during step S102, three dimensional measurement of the solder 3 printed on the circuit board 1 is performed based on the image data stored in the image memory 42. The height data and various corresponding coordinate data are stored in the inspection result and statistical data memory 49 by this means.

Figure 6:
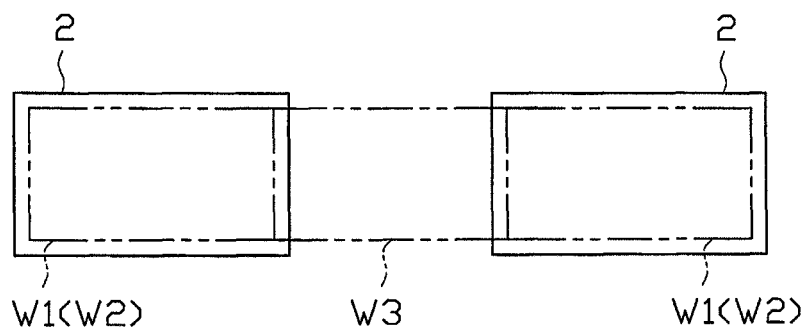
FIG. 6 shows a schematic drawing for explanation of the solder printing region, the solder inspection frame, and the bridge inspection frame according to one or more embodiments of the present invention.

During step S103, solder region (solder clump) extraction processing is performed based on the above-described image data and height data. Specifically, the bridge inspection frame W3 is set in the image data between arbitrary lands 2 (solder printing regions W1) as shown in FIG. 6 based on design data such as Gerber data, etc. stored in the input data memory 47. Next, the above-described height data undergo binarization processing using a certain height level as a threshold value. Then, based on the results of such processing, clump processing is performed for solder clumps above a certain height level, and solder clumps having a surface area greater than a fixed value are detected within the bridge inspection frame W3.

Solder bridge extraction processing is performed during step S104. During this step, solder clumps present between multiple lands 2 (solder inspection frames W2) are extracted as solder bridges 3b (see, FIGS. 7 and 8).

The presence or absence of a solder bridge 3b is determined during step S105. During this step, if not a single solder bridge is determined to exist on the circuit board 1, solder bridge inspection terminates without further processing.

However, if even a single solder bridge 3b is determined to exist on the circuit board 1, during step S106, processing is performed to extract the pair of lands 2 that have the most distant positional relationship among two or more lands 2 contacting a single solder bridge 3b. The detection unit of the present embodiment is especially configured with functions for such processing.

Thereafter, bridge distance calculation processing is performed during step S107. The distance calculation unit is especially configured with functions for such processing. In this context, the minimum distance between two lands extracted during step S106 is calculated as the bridge distance Lx.

Figure 7:
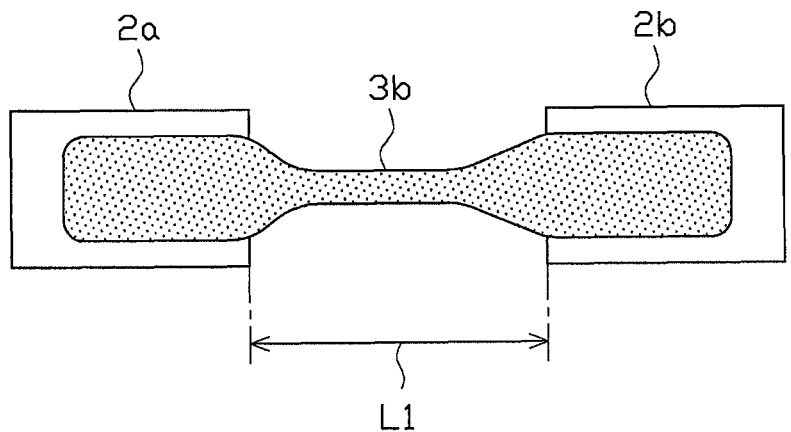
FIG. 7 shows a schematic drawing for explanation of the solder bridge and the bridge distance according to one or more embodiments of the present invention.
Figure 8:
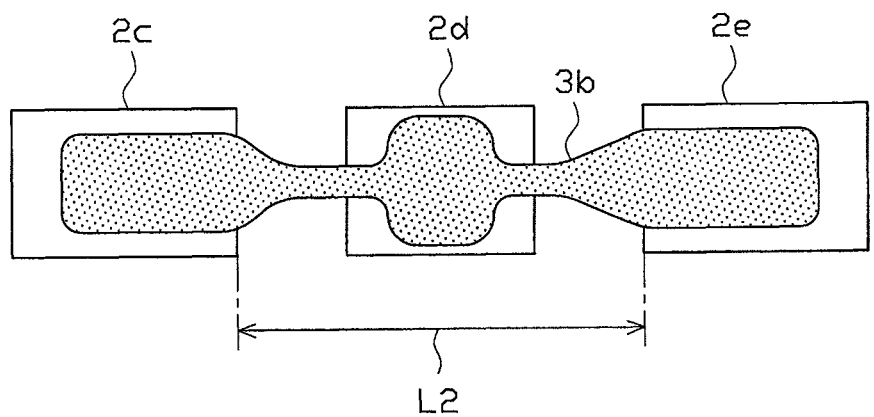
FIG. 8 shows a schematic drawing for explanation of the solder bridge and the bridge distance according to one or more embodiments of the present invention.

For example as shown in FIG. 7, the two lands 2a and 2b correspond to lands having the most distant positional relationship, and the minimum distance L1 between these lands 2a and 2b is calculated as the bridge distance Lx. Moreover, within the example shown in FIG. 8, although the laterally arranged lands 2c and 2e correspond to lands having the most distant positional relationship among the three lands 2c, 2d, and 2e, the minimum distance L2 between these lands 2c and 2e is calculated as the bridge distance Lx. When multiple solder bridges 3b are present on a single circuit board 1, bridge distance calculation processing is repeated only for a number of iterations equivalent to the number of solder bridges 3b.

Whether or not the above-described bridge distance Lx is greater than or equal to the criterion value Lo is determined thereafter during step S108. The distance determination unit of the present embodiment is especially configured with functions for such processing. In the present embodiment, the criterion value Lo is set to 200 μm.

In this context, when the bridge distance Lx is determined to be less than the criterion value Lo, after ordinary bridge defect processing during step 110, solder bridge inspection is terminated.

During ordinary bridge defect processing, defect information relating to the circuit board 1 having the printing defect is sent to a certain ejection mechanism (not illustrated) disposed within the production line. After the ejection mechanism receives this malfunction information, the ejection mechanism ejects from the production line the circuit board 1 pertaining to such malfunction information as a defective product.

Also, during ordinary bridge defect processing, processing is performed to update the number of occurrences of bridge defects stored sequentially in memory by the inspection result, to update the statistical data memory 49 during progress of the solder bridge inspection, and to update the contents of the number of occurrences of such bridge defects displayed on the monitor 51. For example, a histogram (see, FIG. 9) is displayed on the monitor 51 to show the number of occurrences of bridge defects according to the bridge distance Lx (e.g., in 20 μm increments).

On the other hand, when the bridge distance Lx is determined to be greater than or equal to the criterion value Lo during the above-described step S108, after bridge defect severe defect processing is performed during step S109, ordinary bridge defect processing is carried out during step S110 in the above-described manner, and solder bridge inspection is terminated. The step S109 bridge defect severe defect processing corresponds to the severe defect processing in the present embodiment, and the severe defect processing unit is especially arranged with functions for performing such processing.

Figure 9:
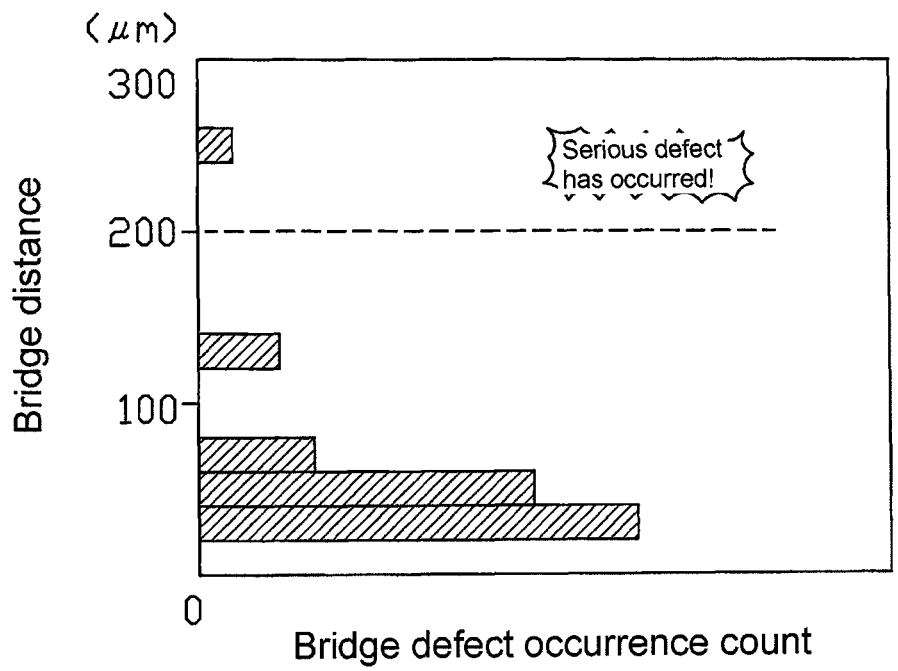
FIG. 9 shows a drawing for explanation of an example of details displayed by the monitor according to one or more embodiments of the present invention.

During the bridge defect severe defect processing, a maintenance request signal as a malfunction signal is set to the solder printing apparatus 12. The solder printing apparatus 12 receiving this maintenance request signal stops the solder printing operation. Also during the bridge defect severe defect processing, processing causes the display of text saying that a "severe defect has occurred" on the monitor 51, as shown in FIG. 9, to provide notification that a severe solder bridge 3b has occurred resulting in a bridge distance Lx exceeding the criterion value Lo. Due to the display of this notification, the operator knows about the generation of the severe solder bridge 3b and, thus, is able to inspect the solder printing apparatus 12 by stopping the solder printing apparatus 12, checking whether the metal mask is contaminated, and the like. Then, after the various types of malfunctions occurring in the solder printing apparatus 12 are fixed, this solder printing apparatus 12 is restarted, and the production line for circuit boards 1 starts up again. When the solder printing apparatus 12 has restarted, a maintenance finished signal is sent from the solder printing apparatus 12 to the solder printing inspection apparatus 13, and solder bridge inspection starts again.

According to the embodiments in accordance with the above-described manner, the extent of the detected solder bridge 3b is determined in addition to detection of the presence-absence of the solder bridge 3b, and, if the solder bridge 3b is relatively minor, production continues without stoppage of the solder printing apparatus 12. When the detected solder bridge 3b is relatively severe, the solder printing apparatus 12 is stopped, and the inspection operation is performed. Due to arrangement of the present embodiment in this manner, it is possible to prevent circumstances whereby production continues for a long time interval while the solder printing apparatus 12 has a severe malfunction. On the other hand, there is no need to stop the solder printing apparatus 12 and wastefully carry out inspection every time a minor solder bridge 3b is detected. As a result, the occurrence of defective products is decreased, yield is improved, and productivity can be improved.

According to one or more embodiments, two lands are extracted that have the most distant positional relationship among the multiple lands contacting a single solder bridge 3b, the minimum distance between those lands 2 is calculated as the bridge distance Lx, and the extent of the solder bridge 3b is determined based on this bridge distance Lx. Due to adoption of this type of configuration, it is possible to calculate the bridge distance Lx based on circuit board design data, such as Gerber data and the like, stored beforehand in the input data memory 47. For this reason, simplification of the processing procedure and improvement of the processing speed are possible in comparison to a configuration whereby the length of the solder bridge 3b is calculated based on various types of data extracted from the image data imaged by the CCD camera unit.

Because setting of the solder inspection frame W2 and the bridge inspection frame W3 is also performed in the present embodiment based on circuit board design data such as Gerber data, etc., the processing procedure is similarly simplified and processing speed is improved, and it is possible to improve inspection efficiency and, thus, improve productivity.

One or more embodiments are arranged to cause the display on the monitor 51 of a histogram showing the number of occurrences of bridge defects according to the bridge distance Lx. By this means, it is possible to readily understand trends in the occurrence of solder bridges 3b and it is possible to use such trend data during performance of adjustment and the like of the solder printing apparatus 12. Furthermore, when a solder bridge 3b is detected that has a bridge distance Lx outside of the permissible range, the operator is able to become aware of the detection of the solder bridge 3b by simply glancing at the monitor.

The present invention is not limited to the mentioned details of the above-described embodiment, and the present invention may be implemented, for example, in the below-described manner.

(a) The above-described embodiments are arranged such that bridge defect severe defect processing (e.g., severe defect processing) includes processing by sending a maintenance request signal to the solder printing apparatus 12 to cause stoppage of the solder printing operation and notification display processing performed using the monitor 51 to indicate that a severe solder bridge 3b has occurred. Severe defect processing is not limited to such processing. For example, when the solder printing apparatus 12 is equipped with a cleaning mechanism for automatically cleaning the metal mask, a configuration is permissible whereby a cleaning request signal is sent to the solder printing apparatus 12. If the solder printing inspection apparatus 13 is equipped with a means for sound generation or the like, a configuration is permissible whereby processing causes the generation of an alarm sound utilizing this means for sound generation.

(b) Although the above-described embodiments are arranged such that the solder bridge 3b is detected by three dimensional measurement, this configuration is not limiting, and detection of the solder bridge 3b by two dimensional measurement is permissible. For example, the solder bridge 3b may be detected by performing binarization of the image data imaged by the CCD camera 33 using a certain brightness value as the threshold value and, then, extracting the regions occupied by the solder 3.

(c) In the above-described embodiments, the bridge distance Lx (e.g., minimum distance between the lands 2) is calculated based on positional information and the like of previously stored design data. However, the method of calculation of the bridge distance Lx is not limited to this method. For example, positional data for each land 2 may be obtained from image data imaged by the CCD camera 33, and the distances for each land 2 may be calculated based upon such positional data.

Figure 10:
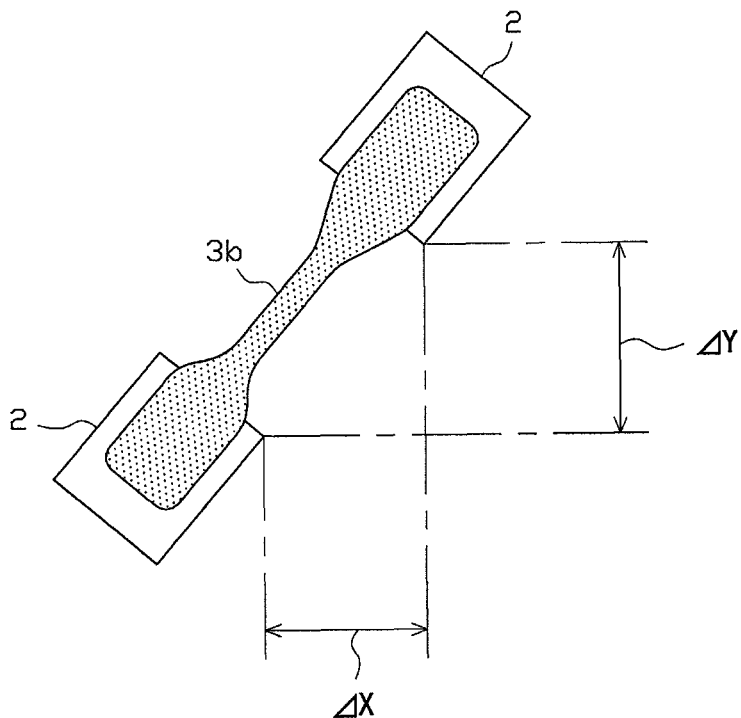
FIG. 10 shows a schematic drawing for explanation of bridge distance according to another embodiment of the present invention.

Moreover, the distance between the two opposing sides of two lands 2 was calculated as the bridge distance Lx (minimum distance between lands 2) in the above-described embodiment. However, this method is not limiting. For example as shown in FIG. 10, the bridge distance Lx may be calculated as the larger value among an X-axis direction distance $\Delta X$ and a Y-axis direction distance $\Delta Y$ between certain points (e.g., centers of gravity or corner parts) of the lands 2. The bridge distance Lx may be calculated as the distance between the certain points $(\Delta X^2+\Delta Y^2)^{1/2}$.

Moreover, rather than the distance between the lands 2, the bridge distance Lx may be calculated as the distance between the solder printing regions W1 or the solder inspection frames W2 set corresponding to these lands 2.

(d) According to the above-described embodiments, setting of the solder inspection frame W2 and the bridge inspection frame W3 is performed based on design data. However, this configuration is not limiting, and the bridge inspection frame W3 and the like may be set based on image data imaged by the CCD camera 33.

(e) According to the above-described embodiments, determination of the extent of the solder bridge 3b is performed for all solder bridges on the circuit board 1. However, this configuration is not limiting, and it is permissible to stop determination processing of the remaining solder bridges when a severe solder bridge 3b has been detected.

(f) According to the above-described embodiments, a maintenance request signal for stopping the solder printing operation is sent to the solder printing apparatus 12 as bridge defect severe defect processing (severe defect processing). However, the solder printing apparatus 12 does not need to be necessarily stopped at this stage, and it is permissible to perform notification display processing so that the operator determines whether or not to stop the solder printing apparatus 12.

(g) The content of the display on the monitor 15 is not limited to the content of the above-described embodiments. For example, the occurrence of bridge defects during a certain time interval or for a certain inspection unit may be displayed as multiple stacked time series plots (as in the content of the display indicated in FIG. 9). By use of this type of display, trends in the occurrence of solder bridges 3b become easily understood.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS

1 . . . circuit board
2 . . . land
3 . . . solder
3b . . . solder bridge
11 . . . solder printing system
12 . . . solder printing apparatus
13 . . . solder printing inspection apparatus
32 . . . illumination device
33 . . . CCD camera
41 . . . control device
43 . . . three dimensional measurement part
44 . . . inspection frame setting part
45 . . . solder region extraction part
46 . . . solder bridge extraction part
47 . . . input data memory
48 . . . calculation processing part
49 . . . inspection result and statistical data memory
51 . . . monitor
Lo . . . criterion value
Lx . . . bridge distance
W1 . . . solder printing region
W3 . . . bridge inspection frame

What is claimed is:
1. A solder printing inspection apparatus for inspection of solder printed on a circuit board having a multiplicity of lands for mounting of electronic components, the solder printing inspection apparatus comprising:
an irradiation unit that irradiates a light on the circuit board;
an imaging unit that images the circuit board irradiated by the light;
a solder bridge detection unit that detects a solder bridge connecting at least two of the lands based on an image data imaged by the imaging unit;
a detection unit that extracts two lands, solder printing regions, or solder inspection frames having a farthest positional relationship among at least two lands contacting a single solder bridge or a solder printing region or solder inspection frame set corresponding to such lands;
a distance calculation unit that calculates, as a bridge distance, a minimum distance between the extracted two lands, solder printing regions, or solder inspection frames;
a distance determination unit that determines whether or not the bridge distance is within a permissible range; and
a severe defect processing unit that performs a certain severe defect processing when the bridge distance is determined not to be within the permissible range,
wherein the solder printing inspection apparatus further comprises a memory unit that remembers various types of setting data relating to manufacture of the circuit board, and the solder bridge detection unit, based on the setting data, sets a bridge inspection frame for detection of the solder bridge.

2. The solder printing inspection apparatus according to claim 1,
wherein the solder printing inspection apparatus further comprises a display unit that displays the detection counts of the solder bridges separately according to the bridge distance.

3. A solder printing system comprising the solder printing apparatus for printing of solder and the solder printing inspection apparatus according to claim 1,
wherein the severe defect processing unit outputs a certain malfunction signal to the solder printing apparatus as the severe defect processing; and
the solder printing apparatus performs a certain processing when the malfunction signal has been input.

* * * * *